United States Patent
Castelo et al.

(10) Patent No.: US 6,575,891 B1
(45) Date of Patent: Jun. 10, 2003

(54) MANUAL RIBBON DELIVERY SYSTEM FOR INTRAVASCULAR RADIATION THERAPY

(75) Inventors: Astor S. Castelo, Miami, FL (US); James L. Janowski, Dania Beach, FL (US); Martin H. Singer, Lauderhill, FL (US); Jeffrey L. Wilkinson, Silver Springs, FL (US)

(73) Assignee: Cordis Corporation, Miami Lakes, FL (US)

( * ) Notice: Subject to any disclaimer, the term of this patent is extended or adjusted under 35 U.S.C. 154(b) by 0 days.

(21) Appl. No.: 09/889,808

(22) PCT Filed: Feb. 15, 2000

(86) PCT No.: PCT/US00/03775

§ 371 (c)(1),
(2), (4) Date: Jul. 20, 2001

(87) PCT Pub. No.: WO00/48661

PCT Pub. Date: Aug. 24, 2000

Related U.S. Application Data (60) Provisional application No. 60/120,231, filed on Feb. 16, 1999.

(51) Int. Cl.[7] .................... A61M 36/00; A61N 5/00
(52) U.S. Cl. ............................................... 600/7
(58) Field of Search ......................... 600/1–8, 424, 600/585

(56) References Cited

U.S. PATENT DOCUMENTS

| | | |
|---|---|---|
| 3,669,093 A | 6/1972 | Sauerwein et al. |
| 4,631,415 A | 12/1986 | Sauerwein et al. |
| 4,851,694 A | 7/1989 | Rague et al. |
| 4,897,076 A | 1/1990 | Puthawala et al. |
| 5,084,001 A | 1/1992 | Van't Hooft et al. |
| 5,139,473 A | 8/1992 | Bradshaw et al. |
| 5,855,563 A | 1/1999 | Kaplan et al. |

*Primary Examiner*—Max F. Hindenburg
*Assistant Examiner*—Brian Szmal
(74) *Attorney, Agent, or Firm*—Michael W. Montgomery (57) ABSTRACT

An afterloader for safely and rapidly advancing a flexible ribbon with a radioactive source (42) through a lumen of a catheter within a patient includes a containment vessel (12), a ribbon extension stop, a ribbon retraction stop, emergency ribbon retraction, ribbon drive mechanism, slip clutch (18), ribbon position indicator (30), security lock mechanism (32), ribbon brake (22), and other novel features.

12 Claims, 8 Drawing Sheets

MANUAL RIBBON DELIVERY SYSTEM FOR INTRAVASCULAR RADIATION THERAPY

This application is a 371 of PCT/US00/03775 Feb. 15, 2000 which claims benefit of 60/120,231 Feb. 16, 1999.

FIELD OF THE INVENTION

The present invention relates to medical devices generally, and to storing, delivering and positioning radioactive ribbons or wires into the body of a patient, which are commonly used in radiation oncology and intravascular radiotherapy. In particular, the present invention relates to such devices, often referred to as "pigs" or "afterloaders." Such devices advance a ribbon having a radioactive source at its distal end along a catheter previously positioned within the body of a patient for a predetermined period of time, and which later withdraw the ribbon from the patient.

BACKGROUND AND SUMMARY OF THE INVENTION

Restenosis after arterial intervention in general, and after percutaneous transluminal coronary angioplasty ("PTCA") in particular, is a concern of physicians practicing PTCA today. Conventional PTCA is performed using a standard balloon catheter such as the type described in U.S. Pat. No. 5,304,197 entitled "Balloons For Medical Devices And Fabrication Thereof," issued to Pinchuk et al. on Apr. 19, 1994, which is incorporated into this disclosure by reference. Balloon catheters are typically used with a guidewire which is inserted into the patient's artery until its distal end is advanced past the diseased or stenotic area of the vessel, where there is a buildup of material. Balloon catheters typically have a guidewire lumen so that the proximal end of the guidewire can be inserted into the distal end of the balloon catheter. Thereafter, the balloon catheter is advanced over the guidewire until the balloon is adjacent the buildup of material, and the balloon is then inflated to compress the buildup. Finally, the balloon is deflated and the catheter is pulled back through the guidewire and removed from the patient's vasculature.

Restenosis of the artery may occur after this procedure, such that the same area of the vessel collapses or becomes clogged again. Recent technology has discovered that treating the diseased area of the vessel with radiation after balloon angioplasty may help prevent restenosis.

Such technology is described in U.S. Pat. No. 5,199,939 issued to Dake et al. on Apr. 6, 1993, entitled "Radioactive Catheter," which is incorporated into this disclosure by reference. Prior technology contemplates the delivery of unspecified doses of radiation via wires having radioactive distal tips. A catheter was inserted into the vasculature and advanced to the site of the previous angioplasty. The radioactive source wire would then be advanced through a lumen in the catheter, so that its radioactive tip is adjacent the diseased site and can deliver the requisite amount of radiation. Thereafter the catheter and wire were removed. Such a device is described in PCT Application PCT/US94/04857, entitled "Radioactive Source Wire, Apparatus And Treatment Methods," published on Nov. 10, 1994 as WO 94/25106.

Because the intensity of the radiation delivered to the vessel wall varies in inverse proportion to the square of the distance between the radioactive source and the vessel wall, it is desirable to center the radioactive wire within the vessel. This is also true when exposing a vessel to a light source. Centering thus prevents areas of the vessel from being overexposed or underexposed to the radiation. One such way to center the radioactive wire would be to deliver the wire to the site via a central lumen of a spiral balloon catheter. An example of a spiral catheter is given in U.S. Pat. No. 4,762,130 issued to Fogarty et al. on Aug. 9, 1988, entitled "Catheter With Corkscrew-Like Balloon," which is incorporated into this disclosure by reference.

It will be appreciated from the foregoing that, in order to accurately position the source wire or ribbon within the patient is desirable. It is also desirable to store the radioactive wire safely when not in use, and to deliver it upon demand. It is known in the medical field of oncology to use afterloader devices in the treatment of cancerous tumors using radioactive sources. Typically one or more catheters are positioned in the patient and then attached to the afterloader, which advances the radioactive source wire along the catheters according to a predetermined sequence calculated to deliver a therapeutic dose of radiation to the tumor. Examples of afterloaders can be found in U.S. Pat. Nos. 5,865,720, Feb. 2, 1999; 5,857,956, Jan. 12, 1999; 5,092,834, Mar. 3, 1992; all of which are incorporated into this disclosure by reference.

The present invention provides for an improved source wire delivery system, or afterloader, which is especially useful for Intravascular Radiation Therapy,("IRT").

The functions of the delivery device include providing for the safe storage, deployment, and retrieval of a ribbon containing radioactive elements. The device provides for the attachment of a special intravascular radiation therapy catheter, through which a drive mechanism extends and retracts the ribbon. In the unlikely event this mechanism fails during retrieval, stranding the radioactive elements outside the containment area, an alternative means of retrieving the ribbon is available. Additional features include a mechanism to restrict unauthorized access and a means to immobilize the ribbon during the treatment period.

These and various other objects, advantages and features of the invention will become apparent from the following description and claims, when considered in conjunction with the appended drawings.

BRIEF DESCRIPTION OF DRAWINGS

The foregoing and other aspects of the present invention will best be appreciated with reference to the detailed description of the invention in conjunction with the accompanying drawings and claims, wherein:

DETAILED DESCRIPTION OF THE PREFERRED EMBODIMENT

The following description of the preferred embodiments of the present invention is merely illustrative in nature, and as such it does not limit in any way the present invention, its application, or uses. Numerous modifications may be made by those skilled in the art without departing from the true spirit and scope of the invention.

The basic construction of the delivery device can best be understood by the following description taken in conjunction with all of the attached drawings. As seen from the drawing figures, the delivery device provides for appearance, structural integrity, and portability. A delivery device according to the principles of the present invention generally consists of a main housing 14, carrying handle 24, and a radiation shielding containment vessel 12.

Figure 1:
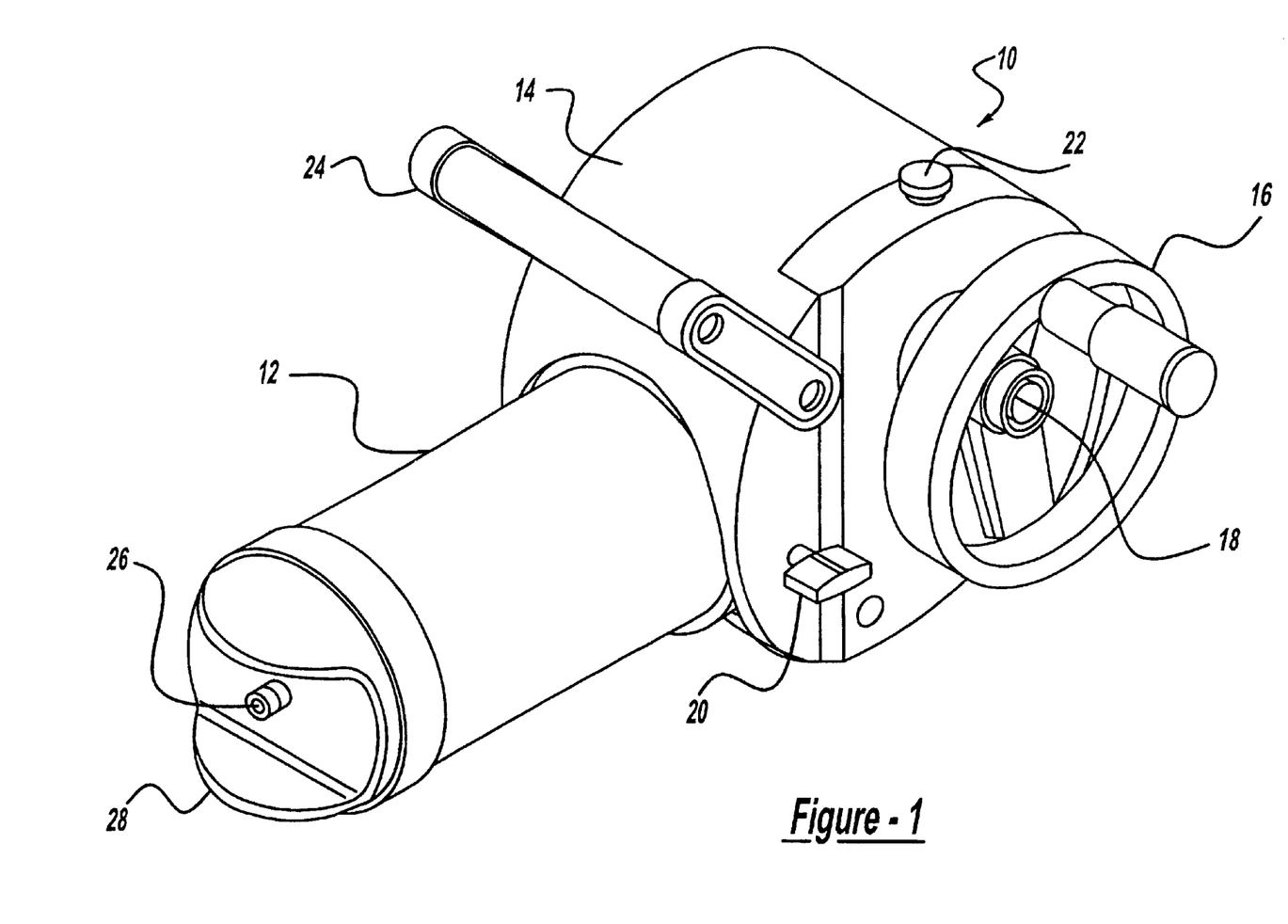
FIG. 1 is a perspective view of a delivery device made in accordance with the principles of the present invention.

Containment Vessel:

The purpose of a delivery device arranged according to the principles of the present invention is to safely hold a relatively long and flexible ribbon having a small bead or radioactive source at a distal end of the ribbon, to rapidly deploy and advance the ribbon and source through a catheter to a desired site for treatment in a patient, and thereafter rapidly withdraw the ribbon and source from the patient into a safe container. Accordingly, one of the most important functions of this device is to provide shielding for the radioactive elements in the ribbon. As shown in FIG. 1, the main shielding component of the delivery device 10 is a removable containment vessel 12, incorporating an inner lead bottle (not shown), an aluminum outer tube, hypotube ribbon guide 34, and end caps. One end cap of the containment vessel has a luer-lock fitting 26 for removably attaching the hub of a catheter, through which the ribbon and radioactive source will travel.

Figure 2:
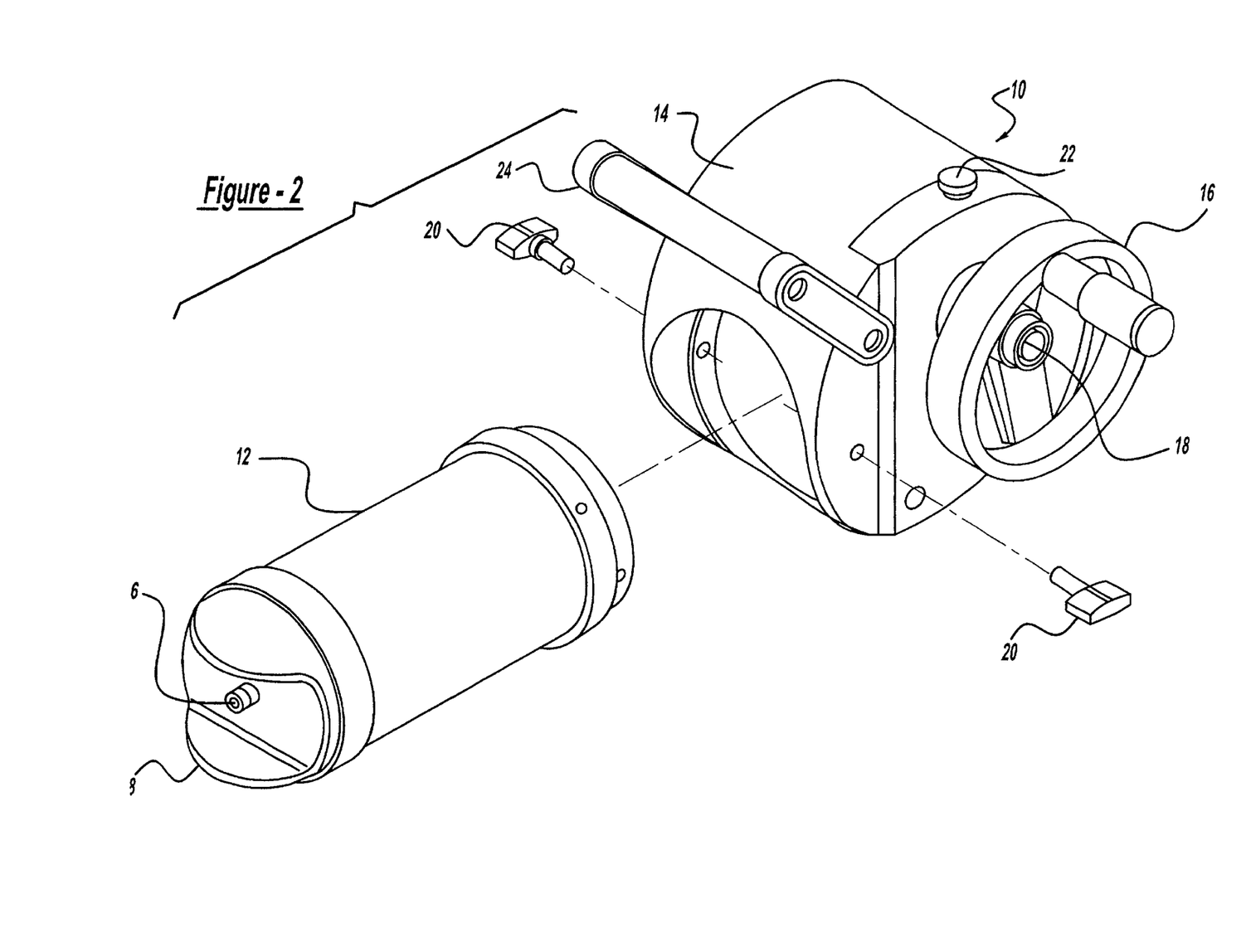
FIG. 2 is a view similar to that of FIG. 1, showing the radiation shielding device and main housing separated.
Figure 3:
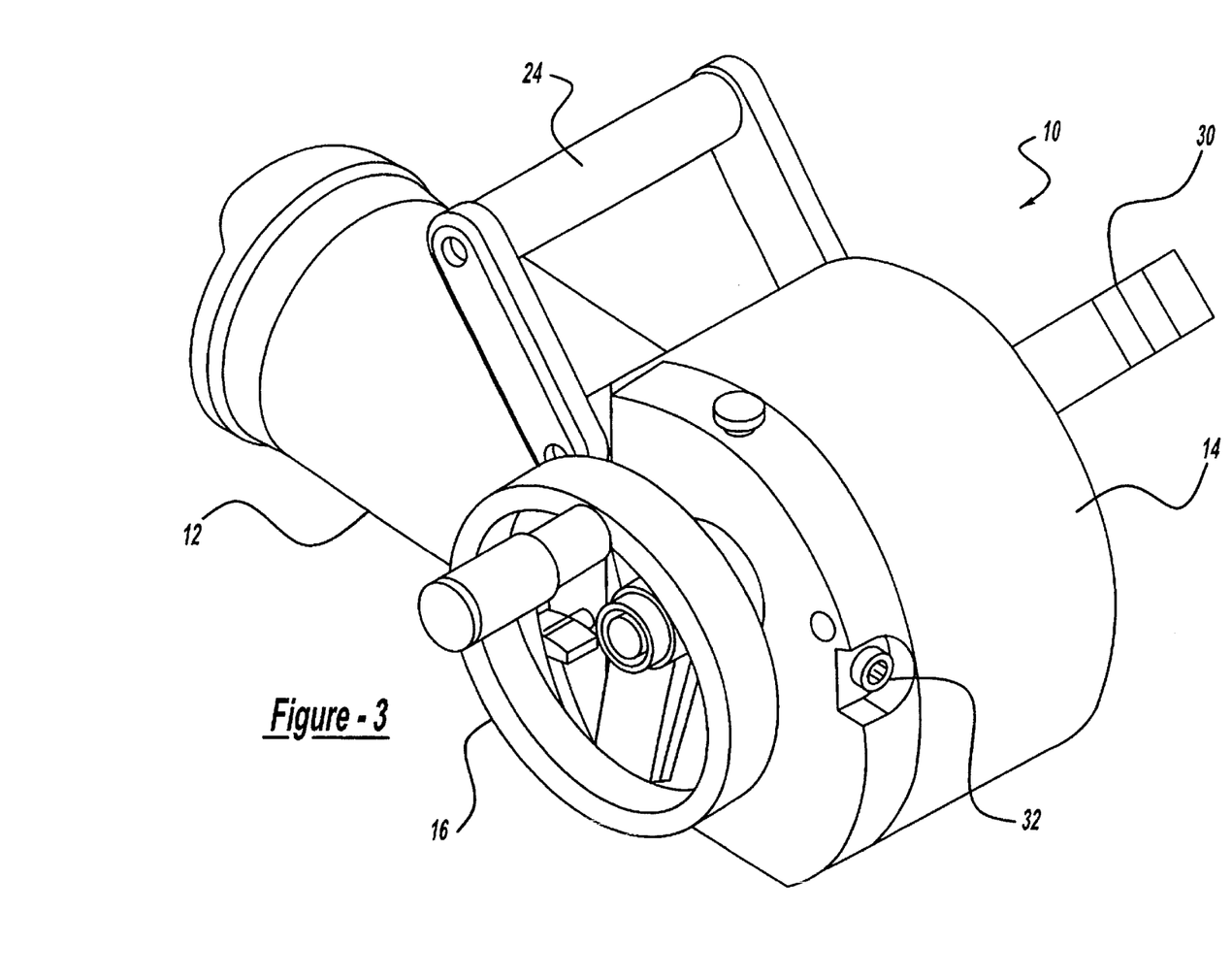
FIG. 3 is a perspective view of a delivery device made in accordance with the present invention shown from an alternate perspective.
Figure 4:
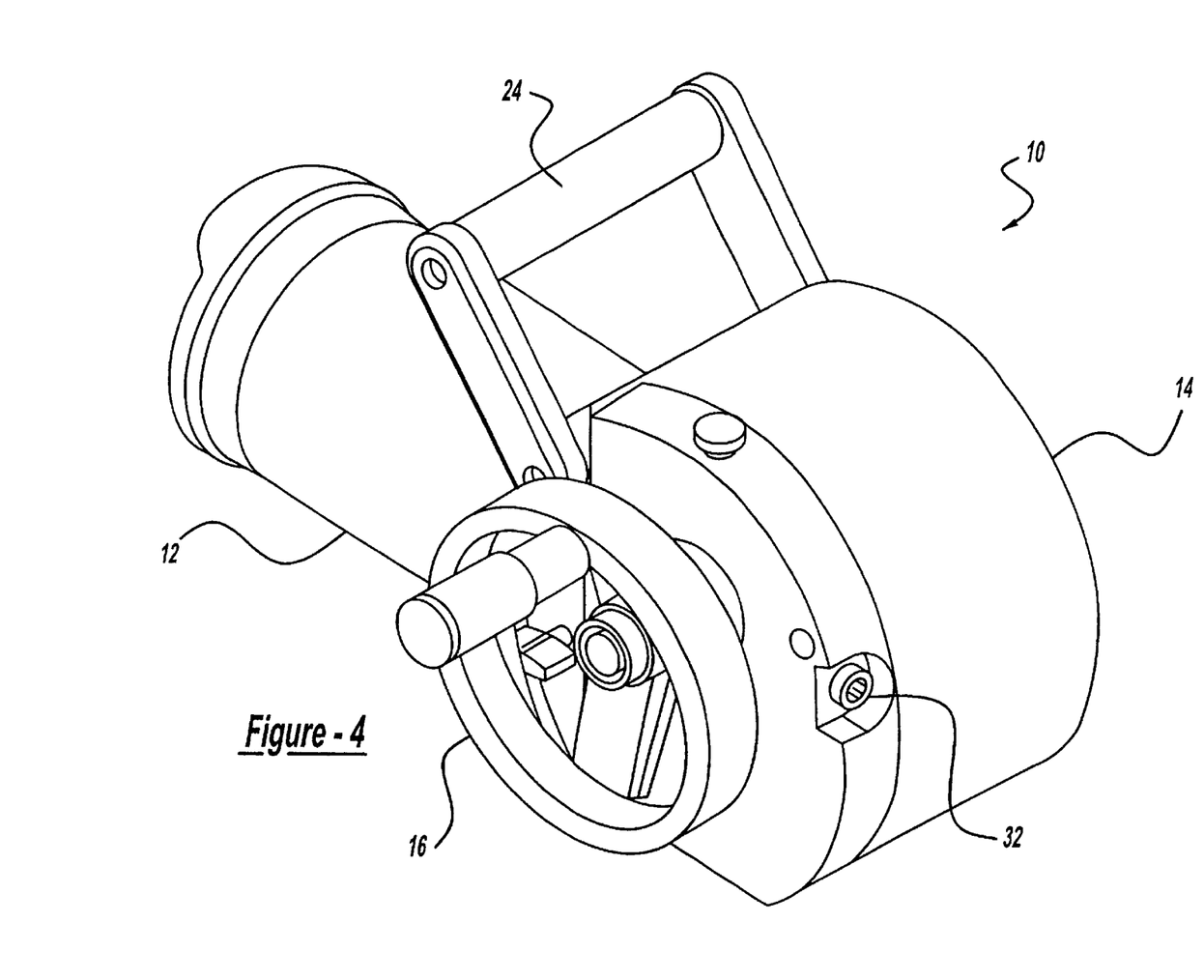
FIG. 4 is a view similar to that of FIG. 3.

This luer-lock fitting 26 is preferably protected by the structure of the end cap. Since the lead shielding is very heavy and may be accidentally dropped, the containment vessel end cap may be provided with flanges 28 as shown in FIGS. 1 and 2, or any other protective configuration, including a shroud, hood or indentation.

For enhanced safety, the containment vessel 12 is preferably attached to a main housing 14 by two quick release fasteners 20. These fasteners 20 allow the containment vessel 12, shielding, and the radioactive source inside to be removed for various reasons. For example, the source may be replaced periodically.

The hypotube ribbon guide 34 has an advanced design which provides for adequate shielding and also low friction when advancing and retracting the ribbon and attached source. In normal operation, the radioactive source should always be within the hypotube 34. Also, the device 10 should preferably provide adequate lead shielding material in all spherical directions around the resting position(s) of the source. Of course, the shielding is easily arranged in all radial directions around the effective axis of the hypotube 34. In addition, the hypotube 34 preferably follows a relatively straight path, with two or more slight bends 36. An example is the configuration of FIG. 5, in which two bends 36 shift the path of the hypotube, so that adequate shielding is provided between the normal resting position for the source and in both proximal and distal longitudinal directions along the effective axis of the hypotube 34.

Figure 5:
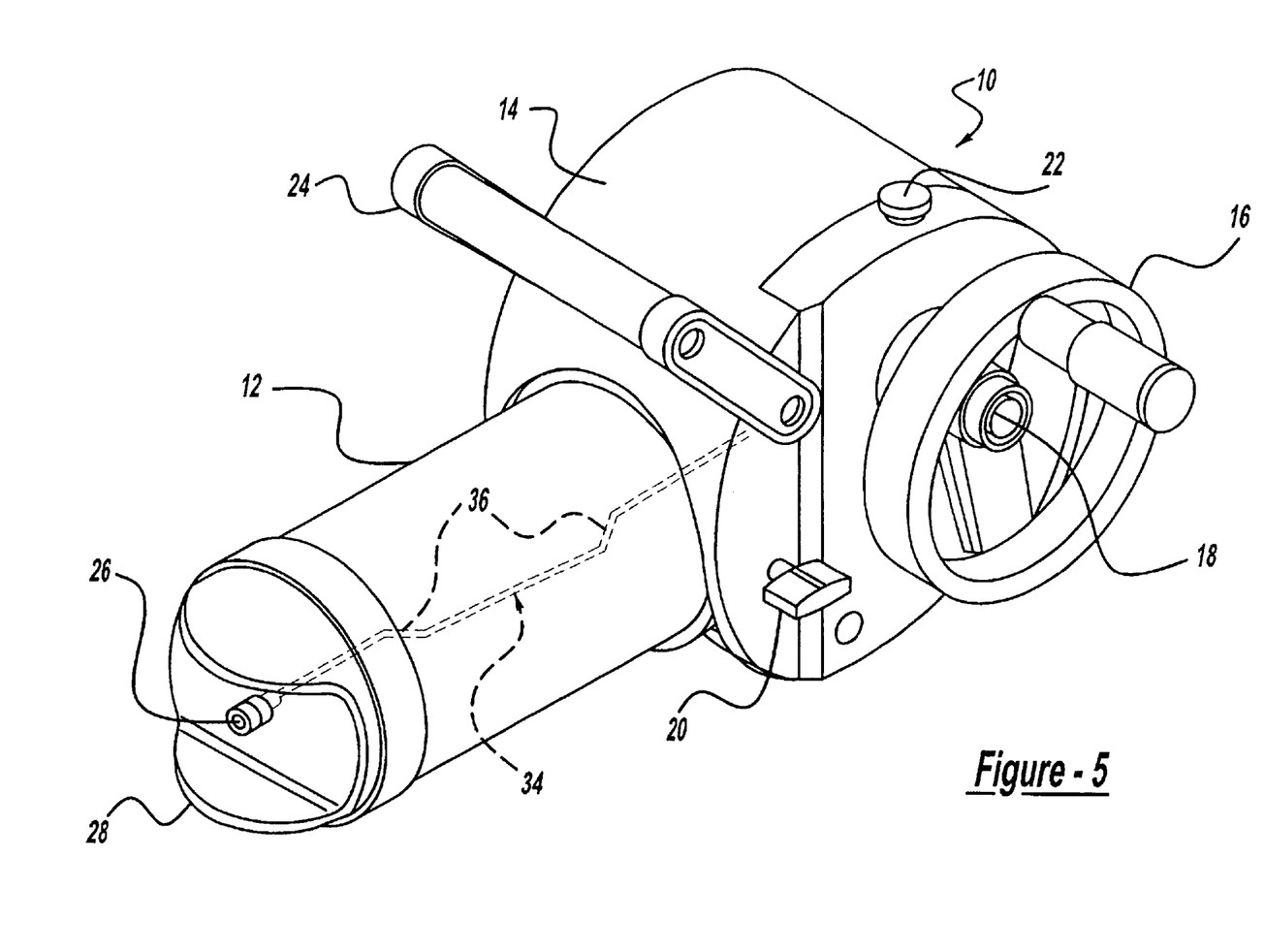
FIG. 5 is a view similar to that of FIG. 1, showing the hypotube.

Because these "shielding" bends 36 are so slight, rather than for example a hypotube with a spiral path, the hypotube 34 presents low friction against rapidly advancing and withdrawing the ribbon and source. The catheter is preferably an intravascular radiation therapy catheter having a lumen to provide a guide within the patient for the ribbon containing the radioactive elements. The luer-lock 26 may be a standard 6 degree screw-lock type.

Ribbon Extension Stop:

A device according to the present invention may preferably have a positive mechanical stop to limit the length of ribbon which can be deployed. This limit is accomplished by adjustable mechanical stops in the ribbon spool, and corresponding adjustable mechanical stops on the main housing, which contact each other after a predetermined number of revolutions of the ribbon spool. These matching stops should be adjustable to account for differing lengths of intravascular radiation therapy catheters.

Ribbon Retraction Stop:

In addition, a positive mechanical stop may preferably be provided, to prevent the radioactive distal portion of the ribbon from being retracted too far, past the radiation shielding containment vessel 12 into the main housing 14. This may be accomplished by adjustable mechanical stops on the ribbon spool, and a removable mechanical stop on the spool spindle. The matching mechanical stops are arranged to contact each other after a predetermined number of revolutions of the ribbon spool 44. This ribbon retraction stop is another safety measure, to avoid the radioactive source 42 from being retracted through and outside the shielding containment vessel 12.

Emergency Ribbon Retraction:

A device arranged according to the present invention may have an alternative means of retrieving the ribbon, providing emergency access to the proximal end of the ribbon. In the unlikely event that the ribbon drive mechanism becomes stuck or otherwise inoperable, the radioactive source may be returned to the containment vessel by allowing the ribbon to be hand- drawn back into the shielded area. Should the drive mechanism become disabled, access to the ribbon is possible by removing two quick-disconnect connectors 20 on the sides of the main housing 14. This configuration allows the radiation shielding 12 and the main housing 14 to be separated, which in turn exposes the proximal portion of the ribbon, allowing for manual retraction into the shielding. The ribbon may also be provided with a variety of marker indications a fixed distance from the source element, so as to determine where to stop manually retracting the ribbon, and thus centering the source in the shielding.

This method for providing emergency access to retract the ribbon is therefore simple, cost effective, reliable, and easy to use.

Figure 6:
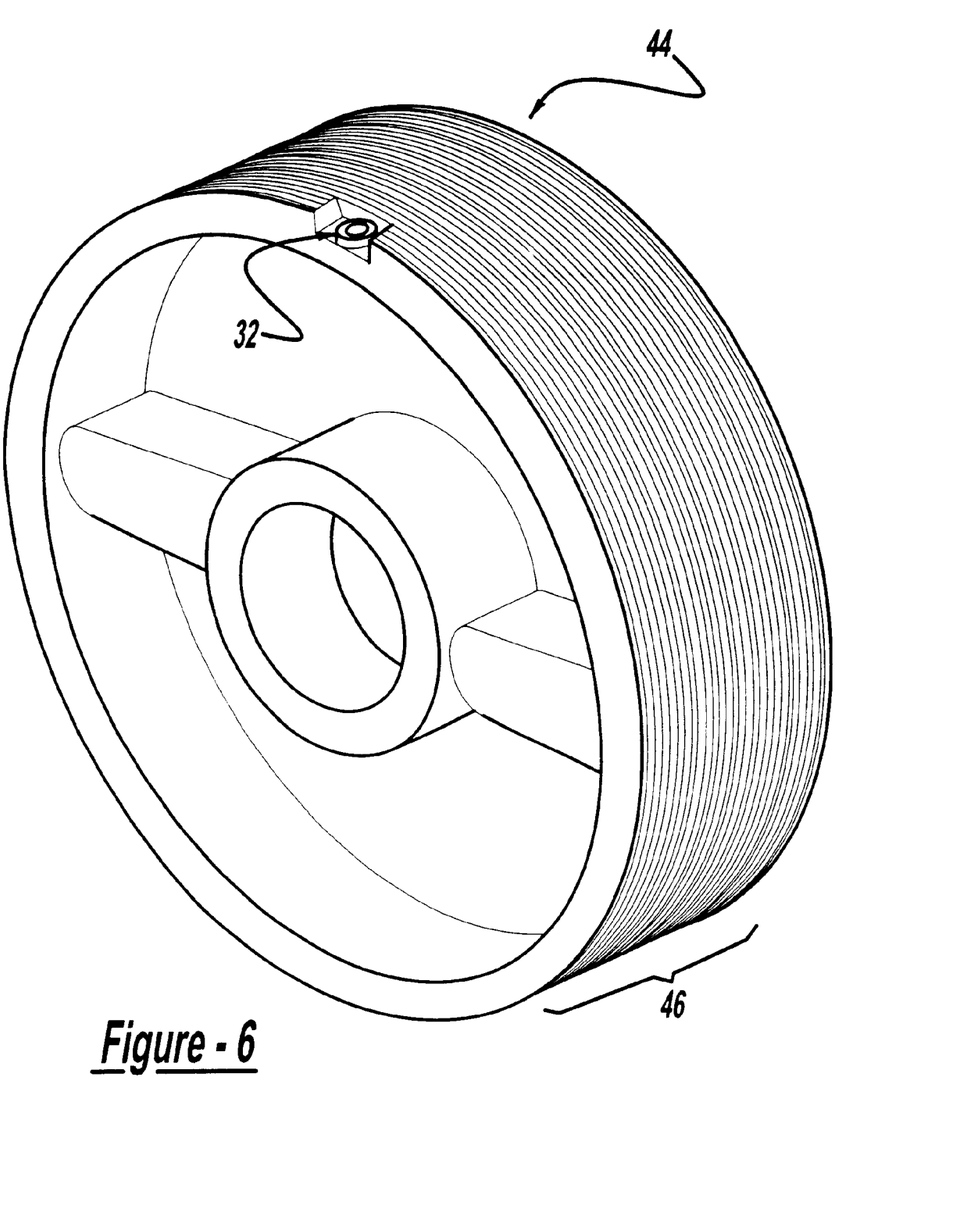
FIG. 6 is a perspective view of a ribbon drive wheel assembly, according to one possible aspect of the present invention.
Figure 7:
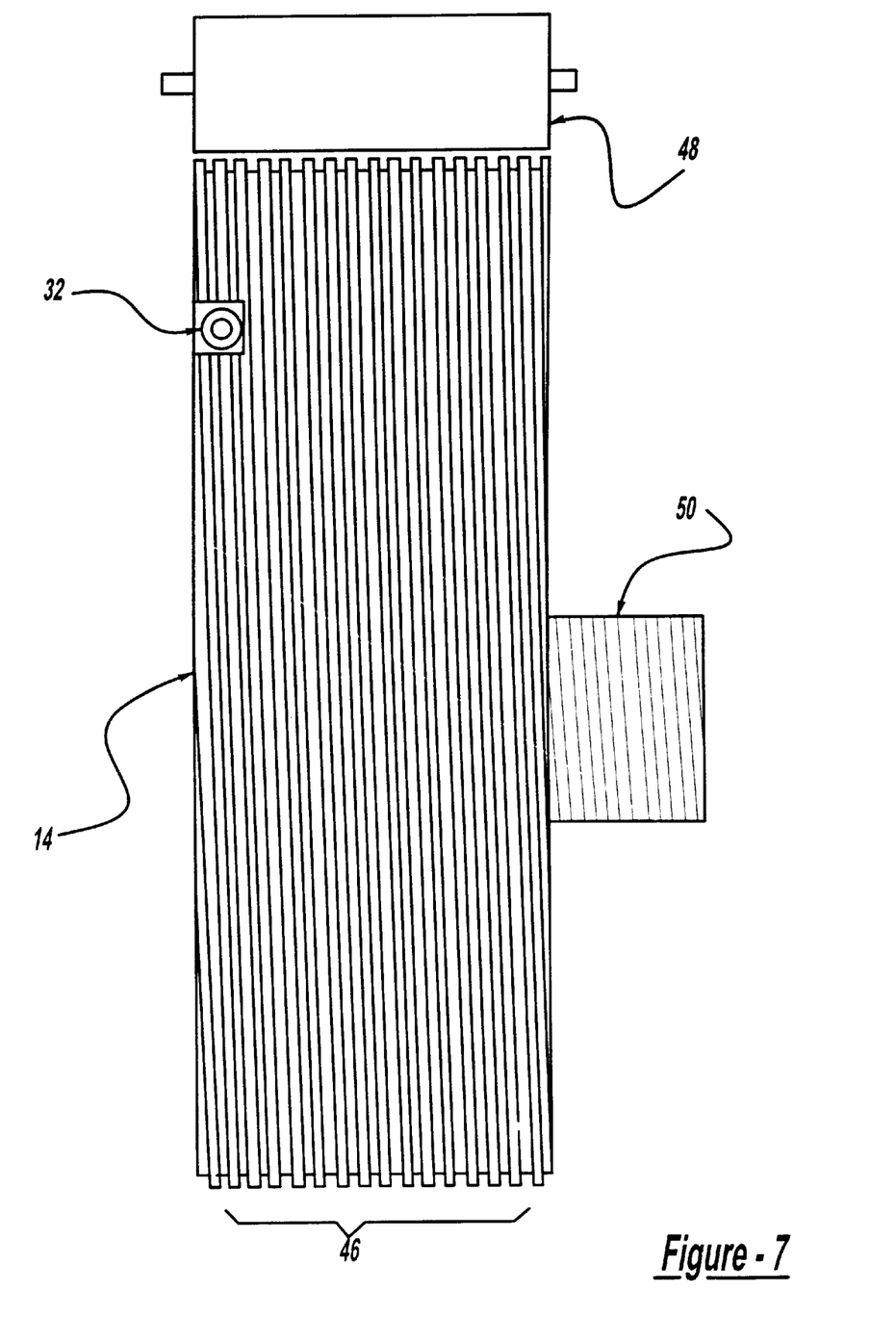
FIG. 7 is a side elevation view of the assembly of FIG. 6.
Figure 8:
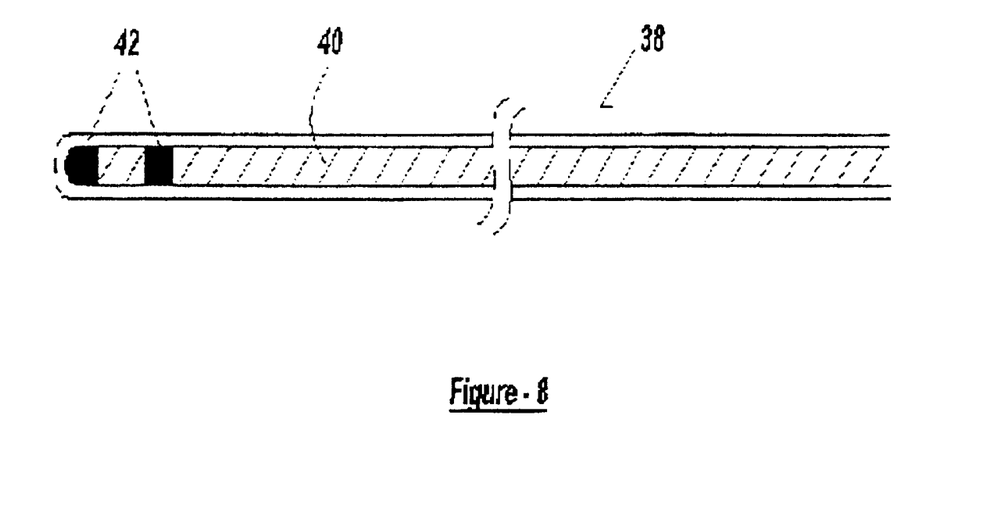
FIG. 8 is a partial cross-section view of a ribbon arranged according to the present invention.

Ribbon Drive Mechanism:

As illustrated in FIG. 8, a ribbon 38 may be formed of a nylon covered, braided steel cable 40 with radioactive source elements 42 at the distal end. The ribbon 38 preferably has an outer diameter between 0.0285" and 0.0305". As shown in FIGS. 6 and 7, a drive mechanism is required to propel the ribbon out of the device, inside the catheter until it reaches the distal end. To accomplish this, the device may include a rotating reel 44 that contains a spiral wound groove 46 on its circumference. The ribbon 38 is loaded onto the reel 44 by guiding it into the groove 46 and pressing it in with a pinch wheel 48. The groove geometry in cross-section is preferably arranged such that, when the ribbon 38 is pressed into the groove 46, the sides of the groove 46 grip the ribbon 38. This allows the reel 44 to apply force on the ribbon during extension. The ribbon 38 is closely guided through the device to prevent it from buckling. The reel groove 46 must maintain alignment with the guide path during extension and retraction of the ribbon 38. To maintain alignment, the reel 44 shifts or translates along its axis during rotation by means of a screw thread 50 arrangement between the reel 44 and its spindle. The thread pitch of the screw thread 50 matches that of the spiral ribbon groove 46.

The driving force for the extension and retraction of the ribbon may be applied by manually rotating a crank assembly 16. The crank assembly 16 is attached to a slip clutch 18, which in turn is attached through an axle to a drive gear assembly. The drive gear assembly applies a rotational force on the reel through two pins on the drive gear, which slide in holes on the reel.

By confining the ribbon 38 within a pathway and gripping it with the reel 44, the mechanism forces the ribbon out through the pathway into the catheter. It is desirable to ensure a solid grip on the ribbon 38 in the groove 46. Given any manufacturing variation in producing the ribbons 38, the groove geometry and resulting pinch force affects performance of this part of the design.

Slip Clutch:

A slip clutch 18 in the drive mechanism may provide a safety function for devices according to the general principles of the present invention. To locate the radioactive source elements 42 in the ribbon 38 at the proper treatment site in the patient, first the intravascular radiation therapy catheter is positioned as needed at the site. The ribbon 38 is then extended into the catheter until it reaches the distal end. The slip clutch 18 is designed as another safety feature, to prevent the ribbon 38 from imparting a force large enough to puncture the catheter when it reaches the distal end, or at any point along the catheter that might be kinked. In addition, by limiting the pushing force, the slip clutch 18 reduces the chances of jamming the drive mechanism. The slip clutch 18 functions by limiting the torque that can be transmitted from the crank assembly 16 to the drive gear.

The slip clutch thus further decreases any possibility of puncturing the catheter or damaging the delivery device.

Ribbon Position Indicator:

The device of the present invention may also provide an approximate indication of the ribbon position during extension and retraction. An indicator 30 extends through the side of the housing 14 and is captive to the spool, as the spool translates back and forth, the position indicator 30 tracks the change in position.

The ribbon position indicator 30 can provide the operator relative position information of the ribbon within the catheter. This allows the operator to deploy the ribbon in an expeditious manner while observing the indicator 30, and providing a visual indication when to slow the deployment of the ribbon to accurately position the radioactive source at the desired site for treatment.

Security Lock Mechanism:

A locking mechanism 32 may be provided to prevent unauthorized use of the device. The mechanism 32 consists of a standard tubular lock and a tapered pin attached to the lock cylinder. When the lock is activated, the tapered pin is captured by the drive gear, which prevents rotation of the ribbon drive mechanism.

Ribbon Brake:

When the ribbon has been positioned properly within the catheter, a ribbon brake 22 may be provided to prevent unintentional movement when the source is deployed within a patient. The brake mechanism 22 is essentially a thumbscrew with a tapered tip. When engaged, the tapered tip is captured by the drive gear which prevents rotation of the ribbon drive mechanism.

The device design allows easy migration of different ribbon diameters for different treatment protocols. Although particular embodiments of the present invention have been shown and described, modification may be made to the device and/or method without departing from the spirit and scope of the present invention. The terms used in describing the invention are used in their descriptive sense and not as terms or limitations.

It should be understood that an unlimited number of configurations for the present invention could be realized. The foregoing discussion describes merely exemplary embodiments illustrating the principles of the present invention, the scope of which is recited in the following claims. Those skilled in the art will readily recognize from the description, claims, and drawings that numerous changes and modifications can be made without departing from the spirit and scope of the invention.

What is claimed is:

1. A system for delivering a flexible ribbon with radioactive source elements to a desired site for medical treatment of a patient, comprising:

a main housing;

a containment vessel removably affixed to the main housing and having a shielding bottle of radioactive shielding material; a hypotube within the containment vessel defining a narrow passage for a ribbon extending from a proximal end to a distal end of the containment vessel; a luer-lock fitting affixed to and communicating with a distal end of the hypotube, for removably attaching a catheter defining a ribbon lumen to the luer-lock fitting;

a quick release mechanism removably affixing the containment vessel to the main housing;

a drive mechanism within the main housing for extending and retracting a ribbon out through the hypotube and luer-lock fitting, including a rotatable reel having a spiral groove for receiving the ribbon; and a flexible ribbon with radioactive source elements at a distal end of the ribbon, mounted about the reel and received in the spiral groove and extending through the hypotube;

such that in the unlikely event the drive mechanism renders the ribbon unretrievable, the quick release mechanism may be actuated to remove the containment vessel from the main housing and exposing the proximal portion of the ribbon, thus allowing the ribbon to be manually retracted until the radioactive source elements are within the containment vessel shielding bottle;

wherein the ribbon exits the groove on the reel at a drive point, the drive point tending to remain at a constant angular position with respect to the main housing, and the drive point tending to shift in a lateral direction parallel to the rotational axis of the reel as the reel rotates and extends or retracts the ribbon, the system further comprising a mechanism for compensating for such shifting of the drive point;

wherein the compensating mechanism further comprises a screw thread having a pitch equal to that of the groove defined by the reel, the reel being mounted about the screw thread such that the reel shifts laterally an equal and opposite distance as the drive point shifts during rotation of the reel.

2. The system set forth in claim 1, further comprising one or more markers on the ribbon, placed a predetermined distance proximal from the radioactive source elements, to remotely indicate when the radioactive source elements are located within the containment vessel shielding bottle.

3. The system set forth in claim 1, further comprising one or more protective structural elements affixed to or defined by the distal end of the containment vessel and extending distally beyond the luer-lock fitting, to protect the luer-lock fitting from damage.

4. The system set forth in claim 1, further comprising one or more first mechanical stops operatively coupled with the reel, and one or more corresponding second mechanical stops coupled to the main housing, arranged such that the first and second stops contact each other after the ribbon is extended a predetermined length by rotating the reel a number of revolutions.

5. The system set forth in claim 4, wherein one or more of the mechanical stops are adjustable, to account for differing lengths of catheters.

6. The system set forth in claim 1, further comprising one or more first mechanical stops operatively coupled with the reel, and one or more corresponding second mechanical stops coupled to the spool spindle, arranged such that the first and second stops contact each other after the ribbon is retracted a predetermined length by rotating the reel a number of revolutions, such that the radioactive source elements are retracted to a normal resting position within but not past the radioactive shielding material.

7. The system set forth in claim 1, further comprising a slip clutch for limiting the maximum torque transmitted from a drive input mechanism to the reel, for additional safety to avoid damage to a catheter affixed to the luer-lock fitting.

8. The system set forth in claim 1, further comprising a security lock mechanism for preventing unauthorized use of the delivery system by selectively locking and preventing rotation of the drive mechanism.

9. The system set forth in claim 1, further comprising a position indicator operatively coupled with the drive mechanism and providing an approximate indication of the extension distance of the ribbon.

10. The system set forth in claim 1, further comprising a brake for selectively locking and preventing movement of the drive mechanism during dwell time of a medical procedure when the ribbon is extended and the radioactive source elements are disposed at the treatment site, to avoid dislodging the radioactive source elements from the treatment site.

11. The system set forth in claim 1, wherein the ribbon further comprises a nylon jacket surrounding a braided metal cable having one or more radioactive source elements at its distal end.

12. The system set forth in claim 1, further comprising a pinch wheel arranged in close proximity to the groove defined by the reel, the pinch wheel being rotatable about an axis parallel to an axis of rotation of the reel, an outer surface of the pinch wheel being spaced a certain distance from the outer surface of the reel, such that the pinch wheel presses the ribbon into the groove and the groove grips the ribbon so as to drive the ribbon in a direction tangent to the groove when the reel is rotated.

* * * * *